United States Patent [19]

Burk

[11] Patent Number: 5,658,897

[45] Date of Patent: Aug. 19, 1997

[54] CYCLOPENTANE(ENE) HEPTANOIC OR CYCLOPENTANE(ENE) HEPTENOIC ACID, 2-HYDROCARBYL PHOSPHINYLOXYALKYL OR PHOSPHONAMIDOALKYL AS THERAPEUTIC AGENTS

[75] Inventor: Robert M. Burk, Laguna Beach, Calif.

[73] Assignee: Allergan, Waco, Tex.

[21] Appl. No.: 629,283

[22] Filed: Apr. 8, 1996

[51] Int. Cl.[6] ............... A61K 31/66; C07F 9/42; C07F 9/44

[52] U.S. Cl. .................. 514/118; 546/22; 549/6; 549/218; 558/190; 558/191; 558/194; 558/195; 558/198; 562/10; 514/89; 514/95; 514/99; 514/114; 514/119; 514/120; 514/127; 514/129

[58] Field of Search .............. 514/118, 119, 514/120, 129; 558/190, 191, 194, 195, 198; 562/10

[56] References Cited

U.S. PATENT DOCUMENTS

| | | |
|---|---|---|
| 4,599,353 | 7/1986 | Bito . |
| 4,994,274 | 2/1991 | Chan et al. . |
| 5,028,624 | 7/1991 | Chan et al. . |
| 5,034,413 | 7/1991 | Chan et al. . |
| 5,288,754 | 2/1994 | Woodward et al. ........... 514/120 X |

FOREIGN PATENT DOCUMENTS

| | | |
|---|---|---|
| 0364417 | 4/1990 | WIPO . |

OTHER PUBLICATIONS

Bito, L.Z., "Prostaglandins, Old Concepts and New Perspectives," Arch Oph., vol. 105, Aug. 1987 pp. 1036–1039.

Bito, L.Z., "Prostaglandins and Related Compounds as Potential Ocular Therapeutic Agents", Biological Protection with Prostaglandins (Cohen, M.M., ed., Boc Raton, FL, CRC Press Inc., 1985, pp. 231–252.

Bito, L.Z., "Prostaglandins, Other Eicosanoids, and Their Derivatives as Potential Antiglaucoma Agents", Applied Pharmacology in the Medical Treatment of Glaucoma, 1984, pp. 477–505.

Nilsson, Siv F.E., et al, "PGF2a Increases Uveoscleral Outflow", ARVO Abstract,, Invest. Ophthalmol. Vis. Sci. 28 (suppl), 1987, p. 284.

Starr, M.S., "Further Studies on the Effect of Prostaglandin on Intraocular Pressure in the Rabbit", Exp. Eye Res., 1971, pp. 170–177.

Siebold et al, "Esterified prostaglandin shows 'potent' promise", Prodrug 5, 1989, pp. 3–4.

Primary Examiner—Johann Richter
Assistant Examiner—Michael G. Ambrose
Attorney, Agent, or Firm—Robert J. Baran; Martin A. Voet; Howard R. Lambert

[57] ABSTRACT

The present invention relates to cyclopentane (or cyclopentane) heptanoic or cyclopentane (or cyclopentene) heptenoic acid, 2-hydrocarbyl phosphinyloxyalkyl or phosphonamidoalkyl, 1-esters, and derivatives thereof, useful as therapeutic agents. In particular, the therapeutic agents of this invention are useful as ocular hypotensives.

21 Claims, 3 Drawing Sheets

CYCLOPENTANE(ENE) HEPTANOIC OR CYCLOPENTANE(ENE) HEPTENOIC ACID, 2-HYDROCARBYL PHOSPHINYLOXYALKYL OR PHOSPHONAMIDOALKYL AS THERAPEUTIC AGENTS

FIELD OF THE INVENTION

The present invention relates to cyclopentane (or cyclopentene) heptanoic or cyclopentane (or cyclopentene) heptenoic acid, 2-hydrocarbyl phosphinyloxyalkyl or phosphonamidoalkyl, 1-esters and other derivatives thereof, which may be substituted in the 3 and/or 5-position of the cyclopentane or cyclopentene ring with hydroxyl or oxo groups, e.g., cyclopentane heptenoic acid, 2-phenylethylphosphonamidomethyl, 3,5-dihydroxy and alkyl esters thereof. The compounds of the present invention are potent ocular hypotensives, and are particularly suitable for the management of glaucoma. Moreover, the compounds of this invention are smooth muscle relaxants with broad application in systemic hypertensive and pulmonary diseases; smooth muscle relaxants with application in gastrointestinal disease, reproduction, fertility, incontinence, shock, etc.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Prostaglandins were earlier regarded as potent ocular hypertensives; however, evidence accumulated in the last two decades shows that some prostaglandins are highly effective ocular hypotensive agents and are ideally suited for the long-term medical management of glaucoma. (See, for example, Starr, M. S., "Further Studies on the Effect of Prostaglandin on Intraocular Pressure in the Rabbit", *Exp. Eye Res.* 1971, 11, pp. 170–177; Bito, L. Z., "Prostaglandins and Related Compounds as Potential Ocular Therapeutic Agents", *Biological Protection with Prostaglandins*, Cohen, M. M., ed., Boca Raton, Fla., CRC Press Inc., 1985, pp. 231–252; and Bito, L. Z., "Prostaglandins, Other Eicosanoids, and Their Derivatives as Potential Antiglaucoma Agents", *Applied Pharmacology in the Medical Treatment of Glaucomas*, Drance, S. M. and Neufeld, A. H. eds., New York, Grune & Stratton, 1984, pp. 477–505). Such prostaglandins include $PGF_{2\alpha}$, $PGF_{1\alpha}$, $PGE_2$, and certain lipid-soluble esters, such as $C_1$ to $C_5$ alkyl esters, e.g. 1-isopropyl ester, of such compounds.

In the U.S. Pat. No. 4,599,353 certain prostaglandins, in particular $PGE_2$ and $PGF_{2\alpha}$ and the $C_1$ to $C_5$ alkyl esters of the latter compound, were reported to possess ocular hypotensive activity and were recommended for use in glaucoma management.

Although the precise mechanism is not yet known, recent experimental results indicate that the prostaglandin-induced reduction in intraocular pressure results from increased uveoscleral outflow (See, for example, Nilsson et al., "$PGF2\alpha$ Increases Uveoscleral Outflow", *Invest. Ophthalmol. Vis. Sci.* 28(suppl), pp. 284 (1987)).

The isopropyl ester of $PGF_{2\alpha}$ has been shown to have significantly greater hypotensive potency than the parent compound, which was attributed to its more effective penetration through the cornea. In 1987 this compound was described as "the most potent ocular hypotensive agent ever reported." (See, for example, Bito, L. Z., Prostaglandins, Old Concepts and New Perspectives", *Arch. Ophthalmol.* 105, pp. 1036–1039, (1987), and Siebold et al., "Esterified prostaglandin shows 'potent' promise", *Prodrug* 5, pp. 3–4 (1989)).

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g. its 1-isopropyl ester, in humans. The clinical potential of prostaglandins in the management of conditions associated with increased ocular pressure, e.g. glaucoma, is greatly limited by these side effects.

Certain phenyl and phenoxy mono, tri and tetra nor prostaglandins and their 1-esters are disclosed in European Patent Application 0,364,417 as useful in the treatment of glaucoma or ocular hypertension.

In a series of co-pending United States patent applications assigned to Allergan, Inc. prostaglandin esters with increased ocular hypotensive activity accompanied with no or substantially reduced side-effects are disclosed. U.S. Pat. No. 5,446,041, relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in U.S. patent application Ser. No. 357,394 (filed 25 May 1989). Similarly, 11,15- 9,15- and 9,11-diesters of prostaglandins, for example 11,15-dipivaloyl $PGF_{2\alpha}$ are known to have ocular hypotensive activity. See U.S. Pat. Nos. 4,494,274; U.S. Pat. No. 5,028,624; U.S. Pat. No. 5,034,413. The disclosures of these patent applications are hereby expressly incorporated by reference.

SUMMARY OF THE INVENTION

We have found that certain cyclopentane(ene) heptanoic or cyclopentane(ene) heptenoic acid, 2-hydrocarbylphosphinyloxy or phosphonamidomethyl compounds and derivatives thereof have pronounced effects on smooth muscle and are potent ocular hypotensive agents.

The present invention relates to methods of treating cardiovascular, pulmonary-respiratory, gastrointestinal, reproductive, allergic disease, shock and ocular hypertension which comprises administering an effective amount of a cyclopentane(ene) heptanoic or cyclopentane(ene) heptenoic acid, 2-hydrocarbyl phosphinyloxymethyl or phosphonamidomethyl compound or derivative thereof represented by the formula I

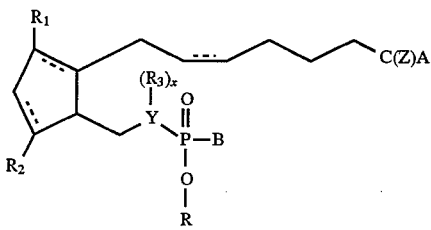

wherein the dashed bonds represent a single bond or a double bond which can be in the cis or trans configuration; A is a radical selected from the group consisting of

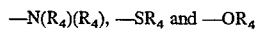

$-N(R_4)(R_4)$, $-SR_4$ and $-OR_4$ wherein $R_4$ is hydrogen or $C_1$ to $C_3$ alkyl; Z is oxo or represents two hydrogen radicals, Y is O or N; x is 0 or 1, provided that x is 0 when Y is O and x is 1 when Y is N; B is an alkyl or an alkylcycloalkyl radical having from one to ten carbon atoms, e.g. about six to eight carbon atoms, or an arylalkyl radical, selected from the group consisting of hydrocarbyl arylalkyl and heteroarylalkyl radicals wherein the heteroatom is selected from the group consisting of nitrogen, oxygen and sulfur atoms and said arylalkyl radical may comprise up to twelve carbon atoms; R is selected from the group consisting of hydrogen; lower alkyl and alkenyl radicals having from 1 to 10 carbon atoms, including cycloalkyl and cycloalkenyl radicals; aromatic radicals, including condensed ring aromatic radicals and heteroaromatic radicals having from 1 to 10 carbon atoms, wherein said heteroatom is selected from the group consisting of oxygen, nitrogen, and sulfur; and substituted derivatives thereof wherein said substituent is X, as defined below; $R_3$ is hydrogen or a lower alkyl radical having from 1 to 3 carbon atoms; and $R_1$ and $R_2$ are as defined below. For example, B may be selected from the group consisting of methyl, ethyl, propyl, butyl, cyclopentylethyl, cyclohexylethyl, phenylethyl, thienylethyl, furanylethyl, pyridylethyl, etc. Moreover, B may be substituted by radicals represented by X, as defined below. R is preferably selected from the group consisting of hydrogen and alkyl radicals having from 1 to 4 carbon atoms.

More preferably the method of the present invention comprises administering a cyclopentane(ene) heptanoic or cyclopentane(ene) heptenoic acid, 2-(phenyl alkylphosphinyloxymethyl or phosphonamidomethyl) compound represented by the formula II

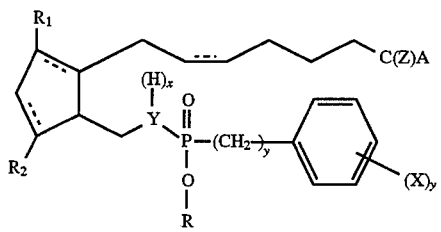

wherein y is 0, or an integer of from 1 to 4, e.g. 1, 2 or 3; X is a radical selected from the group consisting of halo, e.g. fluoro, chloro, etc., nitro, amino, thiol, hydroxy, alkyl, alkyloxy, alkylcarboxy, halo substituted alkyl, e.g. trifluoromethyl radicals, wherein said alkyl comprises from 1 to 3 carbon atoms, etc. and the symbols $R_1$ and $R_2$ are as defined below.

Preferably the compound used in the above method of treatment is a compound of formula (III).

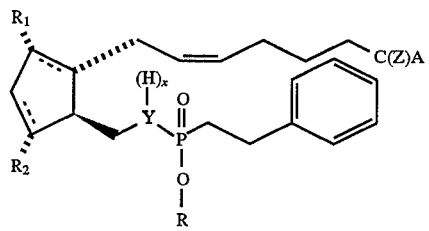

wherein hatched lines indicate α configuration, solid triangles are used to indicate β configuration; one of $R_1$ and $R_2$ is =O, —OH or a —O(CO)$R_6$ group, and the other one is —OH or —O(CO)$R_6$, or $R_1$ is =O and $R_2$ is H; wherein $R_6$ is a saturated or unsaturated acyclic hydrocarbon group having from 1 to about 20 carbon atoms, or —(CH$_2$)$_m$R$_7$ wherein m is 0–10, and $R_7$ is an aliphatic ting from about 3 to about 7 carbon atoms, or an aryl or heteroaryl ring, as defined above; or a pharmaceutically acceptable salt thereof. Preferably $R_1$ and $R_2$ are —OH.

In another aspect, the present invention relates to a method of treating cardiovascular, pulmonary-respiratory, gastrointestinal, reproductive and allergic diseases, shock and ocular hypertension which comprises administering to a subject a pharmaceutical composition comprising a therapeutically effective amount of a cyclopentane heptenoic acid or derivative thereof of formula (IV)

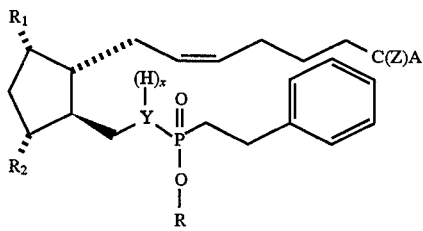

wherein the symbols and substituents are as defined above, in combination with a pharmaceutical carrier.

In a further aspect, the present invention relates to pharmaceutical compositions comprising a therapeutically effective amount of a compound of formulae (I), (II), (III), or (IV) wherein the symbols have the above meanings, or a pharmaceutically acceptable salt thereof in admixture with a non-toxic, pharmaceutically acceptable liquid vehicle.

In a still further aspect, the present invention relates to howl cyclopentane heptenoic acid, 5-cis-2-

(phenylethylphosphinyloxymethyl and phosphonamidomethyl), 3, 5 dihydroxy 1-alkyl esters and other 1-amido or thio derivatives thereof, of the above formulae, wherein the substituents and symbols are as defined hereinabove, or a pharmaceutically acceptable salt of such compounds.

BRIEF DESCRIPTION OF THE DRAWING

Figures

DETAILED DESCRIPTION OF THE INVENTION

Figure 1:
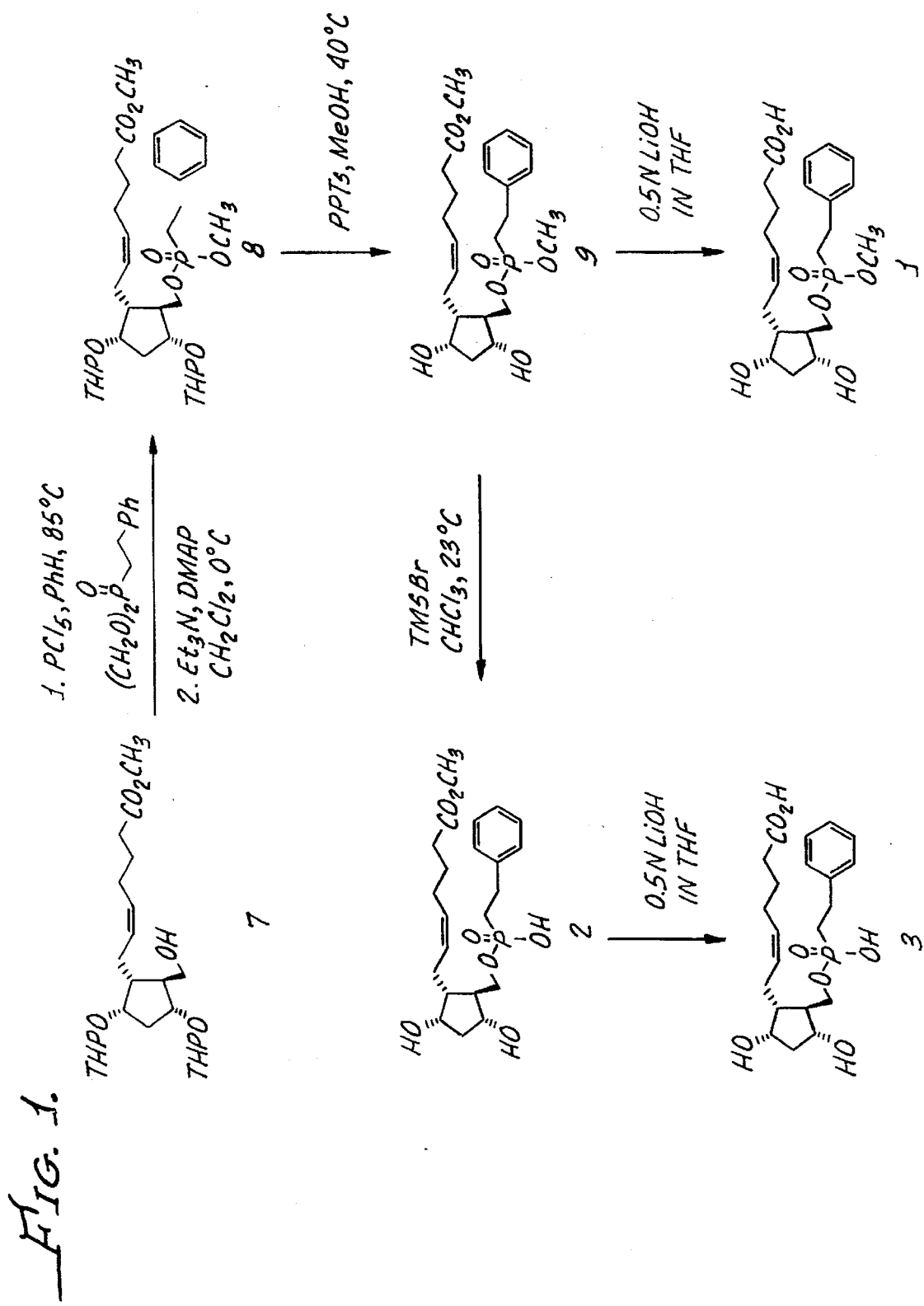
FIG. 1 outlines a general procedure for preparing certain cyclopentane heptenoic acid, 2-phenylethylphosphinyloxymethyl compounds of the present invention.
Figure 2:
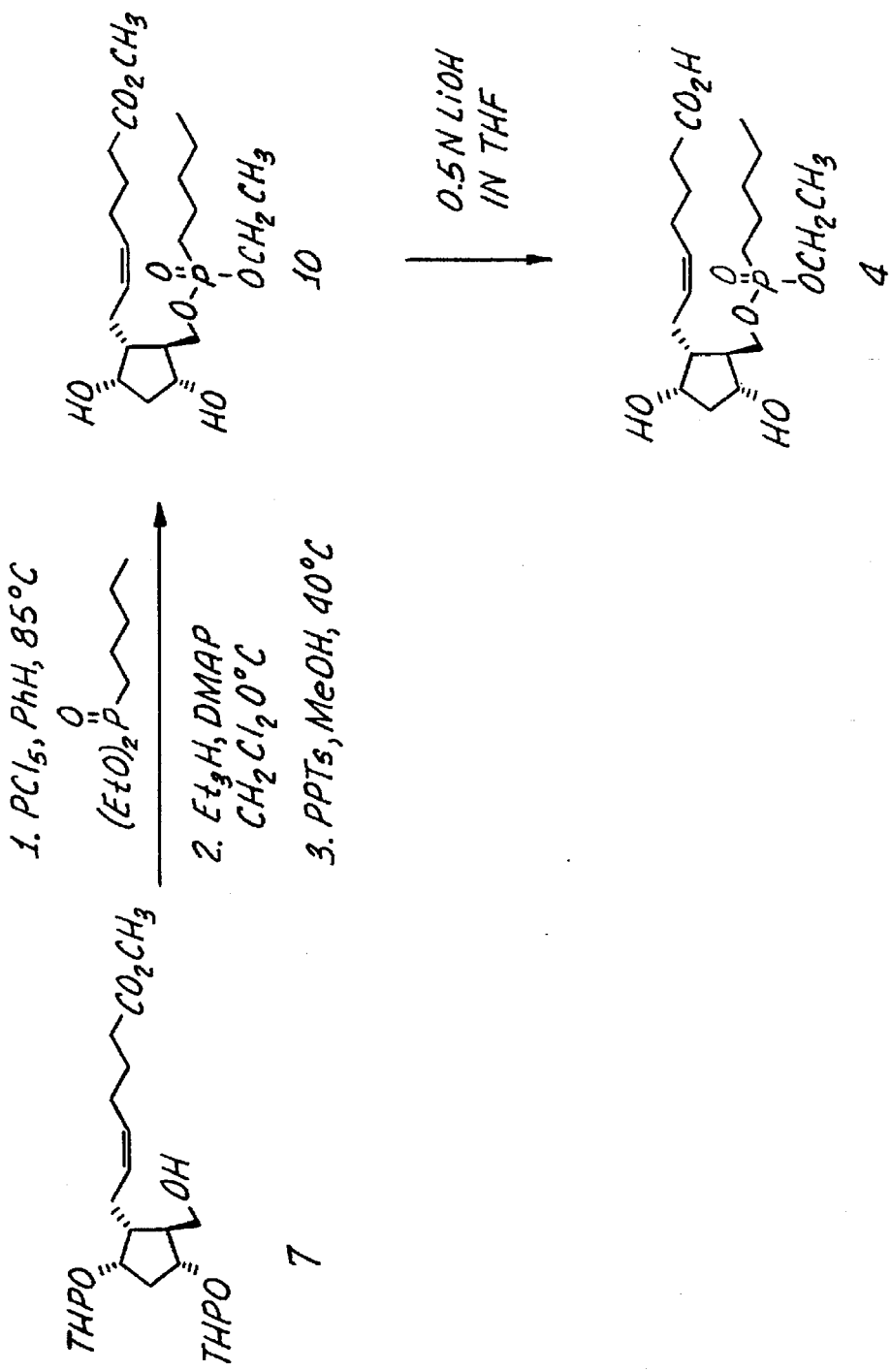
FIG. 2 outlines a general procedure for preparing certain cyclopentane heptenoic acid, 2-pentylphosphinyloxymethyl compounds and 1-alkyl esters thereof of the present invention.
Figure 3:
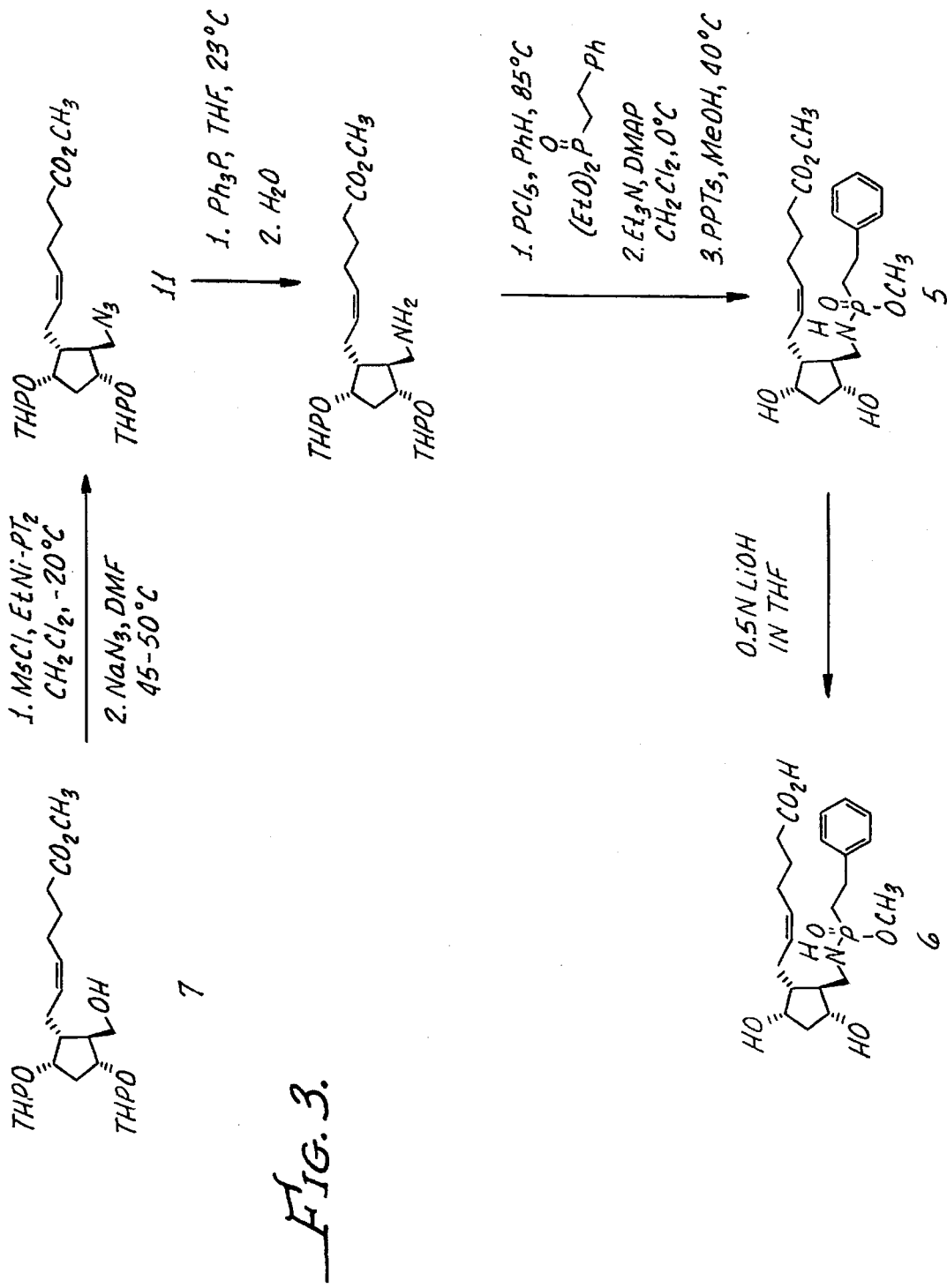
FIG. 3 outlines a general procedure for converting certain cyclopentane heptenoic acid, 2-phenylethylphosphohamidomethyl compounds and 1-alkyl esters thereof of the present invention.

The present invention relates to the use of cyclopentane (ene) heptanoic or cyclopentane(ene) heptenoic acid, 2-hydrocarbyl phosphinyloxymethyl or phosphonamidomethyl compounds and derivatives thereof as therapeutic agents, e.g. as ocular hypotensives. These therapeutic agents are represented by compounds having the formula I,

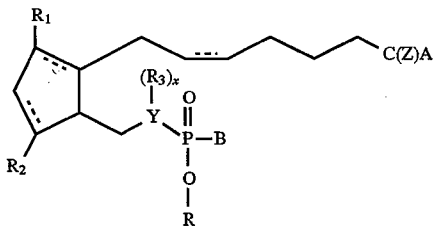

as defined above.

The preferred cyclopentane(ene) heptanoic or cyclopentane(ene) heptenoic acid, 2-(phenylalkylphosphinyloxymethyl and phosphonamido methyl) compounds and derivatives thereof used in accordance with the present invention are encompassed by the following structural formula (II)

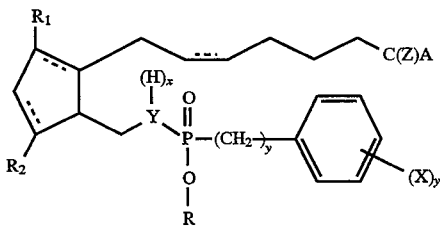

wherein the substituents and symbols are as hereinabove defined.

More preferably the therapeutic agents of the present invention are represented by formula (III).

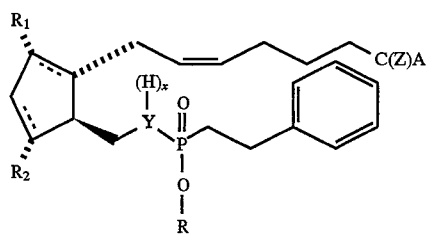

wherein the substituents and symbols are as defined above.

More preferably, the therapeutic agents utilized in the present invention are compounds represented by the formula (IV)

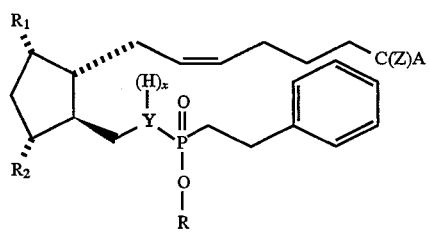

wherein the substituents and the symbols are as defined above.

Most preferably the present invention utilizes the novel compounds of the formula (V)

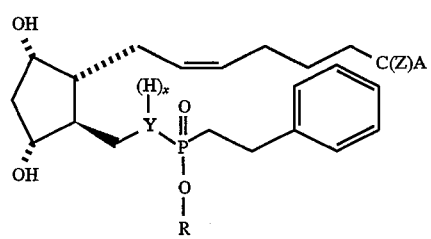

In all of the above formulae, as well as in those provided hereinafter, the lines represent bonds. Where there is no symbol for the atoms between the bonds, the appropriate carbon-containing radical is to be inferred. For example in formula V, the radical between the phenyl ring and the phosphono radical is a methylene ($CH_2$) radical. The radical adjacent the double bond is a CH radical. Moreover, the dotted lines on bonds indicate a single or a double bond which can be in the cis or trans configuration. If two solid lines are used that indicates a specific configuration for that double bond. Hatched lines indicate the α configuration. If one were to draw the β configuration, a solid triangular line would be used.

In the compounds used in accordance with the present invention, compounds having substituents in the α or β configuration are contemplated. As hereinabove mentioned, in all formulas provided herein broken line or hatched attachments to the cyclopentane ring indicate substituents in the α configuration. Thickened solid line or triangle attachments to the cyclopentane ring indicate substituents in the β configuration.

For the purpose of this invention, unless further limited, the term "alkyl" refers to alkyl groups having from one to ten carbon atoms, the term "cycloalkyl" refers to cycloalkyl groups having from three to seven carbon atoms, the term "aryl" refers to aryl groups having from four to ten carbon atoms. The term "saturated or unsaturated acyclic hydrocarbon group" is used to refer to straight or branched chain, saturated or unsaturated hydrocarbon groups having from one to about 6, preferably one to about 4 carbon atoms. Such groups include alkyl, alkenyl and alkynyl groups of appropriate lengths, and preferably are alkyl, e.g. methyl, ethyl, propyl, butyl, pentyl, or hexyl, or an isomeric form thereof. The term "hydrocarbyl" refers to radicals comprising hydrogen and carbon atoms and may have up to 20 carbon atoms. In the "heteroatom-substituted hydrocarbon" the heteroatom-carbon bond replaces either a carbon-hydrogen or a carbon-carbon bond of the above hydrocarbyl radical.

The definition of $R_6$ may include a cyclic component, —$(CH_2)_mR_7$, wherein n is 0–10, $R_7$ is an aliphatic ring from about 3 to about 7 carbon atoms, or an aromatic or heteroaromatic ring. The "aliphatic ring" may be saturated or unsaturated, and preferably is a saturated ring having 3–7 carbon atoms, inclusive. As an aromatic ring, $R_7$ preferably is phenyl, and the heteroaromatic rings have oxygen, nitrogen or sulfur as a heteroatom, i.e., $R_7$ may be thienyl, furanyl, pyridyl, etc. Preferably m is 0–4.

A is preferably selected from the group consisting of:

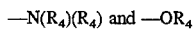

wherein $R_4$ is hydrogen or $C_1$ to $C_3$ alkyl. Z is preferably oxo.

Preferred representatives of the compounds within the scope of the present invention are the compounds of formula V i.e.:

7-[3α,5α-Dihydroxy-2β-[[methoxy(2-phenylethyl)- phosphinyl]oxymethyl]cyclopentyl]-5Z-heptenoic acid 7-[3α,5α-Dihydroxy-2β-[[methoxy(2-phenylethyl) phosphonamido]cyclopentyl]-5Z-heptenoic acid Methyl-7-[3α,5α-dihydroxy-2β-[[methoxy(2-phenylethyl)- phosphonamido]cyclopentyl]-5Z-heptenoate The following novel compounds may be used in the pharmaceutical compositions and the methods of treatment of the present invention.

(1) 7-[3α,5α-Dihydroxy-2β-[[methoxy(2-phenylethyl) phosphinyl]oxymethyl]cyclopentyl]-5Z-heptenoic acid (2) Methyl-7-[3α,5α-dihydroxy-2β-[[methoxy(2-phenylethyl)phosphinyl]oxymethyl]cyclopentyl]-5Z-heptenoate (3) 7-[3α,5α-Dihydroxy-2β-[[methoxy(2-phenylethyl) phosphinyl]oxymethyl]cyclopentyl]-5Z-heptenol (4) 7-[3α,5α-Dihydroxy-2β-[[methoxy(2-phenylethyl) phosphinyl]oxymethyl]cyclopentyl]-5Z-heptenamide (5) 7-[3α,5α-Dihydroxy-2β-[[methoxy(2-phenylethyl) phosphinyl]oxymethyl]cyclopentyl]-5Z-N,N-dimethyl heptenamide (6) 7-[3α,5α-Dihydroxy-2β-[[methoxy(2-phenylethyl) phosphinyl]oxymethyl]cyclopentyl]-5Z- heptenylmethoxide (7) 7-[3α,5α-Dihydroxy-2β-[[hydroxy(2-phenylethyl) phosphinyl]oxymethyl]cyclopentyl]-5Z-heptenoic acid (8) 7-[3α,5α-Dihydroxy-2β-[[ethoxy(2-phenylethyl) phosphinyl]oxymethyl]cyclopentyl]-5Z-heptenoic acid (9) 7-[3α,5α-Dihydroxy-2β-[(methoxy(2-phenylethyl) phosphonamido)methyl]]cyclopentyl]-5Z-heptenoic

(10) Methyl-7-[3α,5α-dihydroxy-2β-[(methoxy(2- phenylethyl)phosphonamido)methyl]cyclopentyl]-5Z- heptenoate

(11) 7-[3α,5α-Dihydroxy-2β-[(methoxy(2-phenylethyl) phosphonamido)methyl]cyclopentyl]-5Z-heptenol

(12) 7-[3α,5α-Dihydroxy-2β-[(methoxy(2-phenylethyl) phosphonamido)methyl]cyclopentyl]-5Z-heptenamide

(13) 7-[3α,5α-Dihydroxy-2β-[(methoxy(2-phenylethyl) phosphonamido)methyl]cyclopentyl]-5Z-N,N-dimethyl heptenamide

(14) 7-[3α,5α-Dihydroxy-2β-[(methoxy(2-phenylethyl) phosphonamido)methyl]cyclopentyl]-5Z-heptenyl methoxide

(15) 7-[3α,5α-Dihydroxy-2β-[(hydroxy(2-phenylethyl) phosphonamido)methyl]cyclopentyl]-5Z-heptenoic acid

(16) 7-[3α,5α-Dihydroxy-2β-[(ethoxy(2-phenylethyl) phosphonamido)methyl]cyclopentyl]-5Z-heptenoic acid

(17) 7-[3α,5α-Dihydroxy-2β-[(ethoxypentylphosphinyl) oxymethyl]cyclopentyl]-5Z-heptenoic methoxide acid A pharmaceutically acceptable salt is any salt which retains the activity of the parent compound and does not impart any deleterious or undesirable effect on the subject to whom it is administered and in the context in which it is administered. Such salts are those formed with pharmaceutically acceptable cations, e.g., alkali metals, alkali earth metals, etc.

Pharmaceutical compositions may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 0–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop usually is about 20–35 μl.

The invention is further illustrated by the following non-limiting Examples wherein the compounds are numbered in accordance with the numbered steps of the reaction schemes set forth in the Drawing Figures.

EXAMPLE 1

Bis-OTHP phosphonate 8

Phosphorous pentachloride (281 mg, 1.35 mmol) was added to a solution of dimethyl 2-phenylethylphosphonate (255 mg, 1.19 mmol) in benzene (PhH) (4.5 mL). The solution was heated to reflux for 2 h, cooled to room temperature, and concentrated in vacuo. The residue was diluted with anhydrous toluene and concentrated in vacuo again. The crude phosphonochloridate was diluted with CH$_2$Cl$_2$ (4.5 mL), cooled to 0°, and treated successively with a solution of 175 mg (0.40 mmol) of the alcohol 7 (Methyl 7-[3α,5α-dihydroxy-2β-hydroxymethyl cyclopent-1α-yl] 5Z-heptenoate) in CH$_2$Cl$_2$ (1.5 mL), of (166 μL, 1.19 mmol) triethylamine (Et$_3$N) and of (14.6 mg, 0.12 mmol) 4-dimethylaminopyridine (DMAP). After 5 minutes the reaction was allowed to warm to room temperature, stirred for 2 h, and diluted with CH$_2$Cl$_2$. The solution was washed with 1N HCl, saturated aqueous NaHCO$_3$, brine, dried over MgSO$_4$, filtered and concentrated in vacuo. The residue was purified by flash column chromatography (FCC) (silica gel; 100% EtOAc) to afford 200.5 mg (81% yield) of 8. (Methyl 7-[3α,5α-bis(tetrahydropyran-2-yloxy)-2β-[[methoxy(2-phenylethyl)phosphinyl]oxymethyl]cyclopentyl]-5Z-heptenoate).

EXAMPLE 2

A solution of phosphonate 8 (200 mg, 0.32 mmol) and pyridinium p-toluenesulfonate (PPTs)(121.5 mg, 0.48 mmol) in methanol (MeOH) (3.2 mL) was heated to 45° for 1 h. The reaction mixture was cooled to room temperature, concentrated in vacuo and the residue was diluted with ethyl acetate (EtOAc). This solution was washed with 1N HCl, saturated aqueous NaHCO$_3$, brine, dried over MgSO$_4$, filtered concentrated in vacuo, followed by FCC (silica gel; 95:5 EtOAc/MeOH) to yield 111 mg of the methyl phosphonate 9 (Methyl 7-[3α,5α-dihydroxy-2β-[[methoxy(2-phenylethyl)phosphinyl]oxymethyl]cyclopentyl]-5Z-heptenoate).

EXAMPLE 3

7-[3α,5α-Dihydroxy-2-β-[[methoxy(2-phenylethyl) phosphinyl]oxymethyl]cyclopentyl]-5Z-heptenoic acid 1

The methyl phosphonate 9 (50 mg, 0.11 mmol) in tetrahydrofuran (THF) (1.3 mL) was treated with lithium hydroxide (0.66 mL of a 0.5N solution, 0.33 mmol). After 16 h the reaction mixture was acidified With 1N HCl and extracted with EtOAc. The organic portions were combined, washed twice with brine, dried over MgSO$_4$, filtered and concentrated in vacuo. The residue was purified by FCC (silica gel, 4:1 EtOAc/MeOH) to yield 32.0 mg of the title compound 1.

EXAMPLE 4

Methyl 7-[3α,5α-dihydroxy-2-β-[[hydroxy(2-phenylethyl)phosphinyl]oxymethyl]cyclopentyl]-5Z-heptenoate 2

Bromotrimethylsilane (TMSBr) (20 μL, 0.152 mmol) was added to a solution of the methyl phosphonate 9 (50 mg, 0.11 mmol) in anhydrous CHCl$_3$ (1.0 mL) at 23° C. After 16 h the reaction was concentrated in vacuo and purified by flash column chromatography (silica gel; 9:1 EtOAc/MeOH followed by 1:1 EtOAc/MeOH) to provide 42.8 mg of the title compound 2

EXAMPLE 5

7-[3α,5α-Dihydroxy-2-β-[[hydroxy(2-phenylethyl) phosphinyl]oxymethyl]cyclopentyl]-5Z-heptenoic acid 3

A solution of the ester 2 (29 mg, 0.066 mmol) and lithium hydroxide (0.4 mL of a 0.5N solution in H$_2$O, 0.20 mmol) in THF (0.8 mL) was stirred at 23° C. for 24 h. The reaction was quenched with 1M HCl (0.20 mL, 0.20 mmol) and extracted with EtOAc. The organic portion was washed with brine, dried over anhydrous Na$_2$SO$_4$, filtered, concentrated in vacuo, and purified by use of (1:1 EtOAc/MeOH) to yield 22 mg (78%) of the title compound 3 as a white powder.

EXAMPLE 6

7-[3α,5α-Dihydroxy-2β-[ethoxypentylphosphinyl] oxymethyl]cyclopentyl]-5Z-heptenoic acid 4

The title compound is synthesized according to the procedures described above for the synthesis of the phosphonate 1, except that diethyl pentylphosphonate is used instead of dimethyl 2-phenyl ethyl phosphonate. Thus, the alcohol 7 (284 mg, 1.36 mmol) was converted to 25 mg of the title compound.

EXAMPLE 7

Methyl-7-[3α,5α-dihydroxy-2β-methoxy(2-phenylethyl)phosphonamido)methyl]cyclopentyl]-5Z-heptenoate 5

A solution of the alcohol 7 (450 mg, 1.02 mmol) and diisopropylethylamine (EtNi—Pr$_2$)(0.36 mL, 2.04 mmol) in CH$_2$Cl$_2$ (5.1 mL) was cooled to −10° C. Methanesulfonyl chloride (MsCl) (87 μL, 1.13 mmol) was added and the reaction was stirred an additional 1 h. The reaction solution was transferred to a separatory funnel, diluted with CH$_2$Cl$_2$, and then washed with cold 1N HCl, saturated aqueous NaHCO$_3$ and brine. The organic portion was dried over Na$_2$SO$_4$, filtered and concentrated in vacuo.

The crude residue was diluted with dimethylformanide (DMF) (4.5 mL) and sodium azide (NAN$_3$) (99.5 mg, 1.53 mmol) was added. The reaction was heated to 50° C. for 16 h, cooled to room temperature, and diluted with Et$_2$O. After washing with H$_2$O, twice, the organic portion was dried over MgSO$_4$, filtered and concentrated in vacuo. Flash column chromatography of the resulting product (silica gel, 4:1 hex/EtOAc) afforded 356.3 mg (75%) of azide 11.

Triphenylphosphine (Ph$_3$P)(201 mg, 0.77 mmol) was added to a solution of azide 11 (356.3 mg, 0.77 mmol) in anhydrous THF (1.5 mL). After 16 h H$_2$O (21 μL, 1.15 mmol) was added and the reaction was stirred an additional 4 h at 23° C. The reaction solution was diluted with EtOAc and washed with brine. The organic portion was dried over MgSO$_4$, filtered and concentrated in vacuo to provide the amine 12 as a viscous brown oil.

A solution of phosphorous pentachloride (380 mg, 1.82 mmol) and dimethyl 2-phenylethylphosphonate (355 mg, 1.82 mmol) in benzene (4.5 mL) was heated to reflux for 2 h. The reaction was concentrated, diluted in vacuo with toluene (5 mL) and reconcentrated. The residue was kept under vacuum (0.5 mm Hg) for 12 h.

The resulting crude phosphonochloridate was diluted with CH$_2$Cl$_2$(4.5 mL) and cooled to 0° C. A solution of the amine 12 (243 mg, 0.55 mmol) in CH$_2$Cl$_2$ (1.5 mL was added followed by triethylamine (0.23 mL, 1.66 mmol) and then 4-dimethylaminopyridine (20.3 mg, 0.17 mmol). After 15 minutes the reaction was allowed to stir for 72 h, concentrated in vacuo and purified by flash column chromatography (silica gel, 95:5 EtOAc/MeOH) to give 100 mg of a bis-THP protected phosphonamide.

The bis-THP phosphonamide and pyridinium p-toluenesulfonate (278 mg, 1.01 mmol) in MeOH (2.2 mL) was heated to 45° C. for 4 h. The reaction was concentrated in vacuo, diluted with EtOAc, and washed with 1N HCl. The organic portion was separated, washed with brine, dried over MgSO$_4$, filtered and concentrated in vacuo. Purification by FCC (silica gel, 9:1 EtOAc/MeOH) gave 40.1 mg the title compound 5.

EXAMPLE 8

7-[3α,5α-Dihydroxy-2-β-[[methoxy(2-phenylethyl) phosphonamido]methyl]cyclopentyl]-5Z-heptenoic acid 6

A mixture of the title compound 5 of Example 8 (20 mg, 0.044 mmol) and lithium hydroxide (0.26 mL of a 0.5N aqueous solution 0.13 mmol) in THF (0.52 mL) was stirred at 23° C. for 12 h. The reaction mixture was acidified with 1N HCl and extracted with EtOAc. The organic portion was washed, twice, with brine, dried over MgSO$_4$, filtered and concentrated in vacuo. Purification by FCC (silica gel, 2:1 EtOAc/MEOH) yielded 4.9 mg of the title compound 6.

Certain of the above compounds were tested for activity in the various in vitro assays described below and the results are reported in Table 1 below.

TABLE 1

| AGN-# | FP | EC$_{50}$ (nM) EP$_1$ | EP$_3$ | IC$_{25}$ DP/EP$_2$ | EP$_4$ | FP/EP$_4$ Ratio | TP | Platelets aggreg inhib | Dog IOP Monkey (1 day) (5 day) | IOP Hyp/ Miosis |
|---|---|---|---|---|---|---|---|---|---|---|
| 1 | 195 | 10$^4$ | 575 >10$^4$ | | | | | >10$^4$ | | |
| 2 | >10$^4$ | NA | >10$^4$ >10$^4$ | | | 365 NA | >27 | | | |

TABLE 1-continued

| AGN-# | EC$_{50}$ (nM) FP | EP$_1$ | EP$_3$ | DP/EP$_2$ | IC$_{25}$ EP$_4$ | FP/EP$_4$ Ratio | TP | Platelets aggreg inhib | Dog IOP Monkey (1 day) (5 day) | IOP Hyp/ Miosis |
|---|---|---|---|---|---|---|---|---|---|---|
| 3 | >10$^4$ | | | | | | | | | |
| 4 | >10$^4$ | | | | 66318 | >0.15 | | | | |
| 5 | 252 | >10$^4$ | | | | | >10$^4$ | | | |
| 6 | 2140 | | | | 767 | 2.8 | | | | |

Activity at different prostanoid receptors was measured in vitro in isolated smooth muscle preparations. FP-activity was measured as contraction of the isolated feline iris sphincter. EP$_4$-activity was measured as relaxation of smooth muscle of isolated rabbit jugular vein. TP-vasoconstrictor activity was measured as contraction of rings of the isolated rat thoracic aorta. Effects on platelets from healthy human donors were measured by incubating platelet-rich plasma with the compounds described herein. Inhibition of aggregation was determined by the ability of the compounds described herein to inhibit platelet aggregation in platelet-rich plasma induced by 20 µM adenosine diphosphate (ADP).

Potential therapeutic applications of the compounds described above are in osteoporosis, constipation, renal disorders, sexual dysfunction, baldness, diabetes, cancer and in disorder of immune regulation.

Many examples also have pronounced activity at the FP receptor, provisionally termed FP$_{VASC}$ associated with the vascular endothelium in the rabbit jugular vein preparation. Since such agents would be vasodilators they have potential in hypertension and any disease where tissue blood perfusion is compromised. Such indications include, but are not limited to, systemic hypertension, angina, stroke, retinal vascular diseases, claudication, Raynauds disease, diabetes, and pulmonary hypertension.

The effects of certain of the compounds of the working examples on intraocular pressure are also measured. The compounds of Examples 3 and 7 are prepared at 0.1% w/v concentration in a vehicle comprising 0.1% polysorbate 80 and 10 mM tris (hydroxy methyl) aminomethane hydrochloride (TRIS) base. Dogs are treated by administering 25 µl to the ocular surface, while the contralateral eye receives vehicle as a control. Intraocular pressure is measured by applanation pneumatonometry. Dog intraocular pressure is measured immediately before drug administration and at 2, 4, 6 and 24 hours thereafter. Each of the compounds tested lower intraocular pressure in the dog model. See Table 2, below, for this data.

TABLE 2

EFFECT OF AGN 192447 AND AGN 192514 ON DOG IOP

| COMPOUND | Decrease in IOP (mm Hg) at predetermined time points (HR) | | | |
|---|---|---|---|---|
| (Dose) | 2 | 4 | 6 | 24 |
| Example 3 (0.1%) | −1.1 | −2.9 | −3.5 | 0.4 |
| Example 7 (0.1%) | −3.3 | −4.1 | −5.1 | −3.5 |

The compounds of the invention may also be useful in the treatment of various pathophysiological diseases including acute myocardial infarction, vascular thrombosis, hypertension, pulmonary hypertension, ischemic heart disease, congestive heat failure, and angina pectoris, in which case the compounds may be administered by any means that effect vasodilation and thereby relieve the symptoms of the disease. For example, administration may be by oral, transdermal, parenterial, subcutaneous, intravenous, intramuscular, intraperitoneal, transdermal, or buccal routes.

The compounds of the invention may be used alone, or in combination with other of the known vasodilator drugs.

The compounds of the invention may be formulated into an ointment containing about 0.10 to 10% of the active ingredient in a suitable base of, for example, white petrolatum, mineral oil and petrolatum and lanolin alcohol. Other suitable bases will be readily apparent to those skilled in the art.

The pharmaceutical preparations of the present invention are manufactured in a manner which is itself known, for example, by means of conventional dissolving or suspending the compounds, which are all either water soluble or suspendable. For administration in the treatment of the other mentioned pathophysiological disorders. The pharmaceutical preparations which can be used orally include push-fit capsules made of gelatin, as well as soft, sealed capsules make of gelatin and a plasticizer such as glycerol or sorbitol. The push-fit capsules can contain the active compounds in liquid form that may be mixed with fillers such as lactose, binders such as starches, and/or lubricants such as talc or magnesium stearate and, optionally, stabilizers. In soft capsules, the active compounds are preferably dissolved or suspended in suitable liquids, such as in buffered salt solution. In addition, stabilizers may be added.

In addition to being provided in a liquid form, for example in gelatin capsule or other suitable vehicle, the pharmaceutical preparations may contain suitable excipients to facilitate the processing of the active compounds into preparations that can be used pharmaceutically. Thus, pharmaceutical preparations for oral use can be obtained by adhering the solution of the active compounds to a solid support, optionally grinding the resulting mixture and processing the mixture of granules, after adding suitable auxiliaries, if desired or necessary, to obtain tablets or dragee cores.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as inders such as starch, paste using for example, maize starch, wheat starch, rich starchy, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, crosslinked polyvinyl pyrrolidone, agar, or algenic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which if desired, are resistant to gastric juices. For this purpose, concentrated sugar solutions may be used, which may optionally containing gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Suitable formulations for intravenous or parenteral administration include aqueous solutions of the active compounds. In addition, suspensions of the active compounds as oily injection suspensions may be administered. Aqueous injection suspensions may contain substances which increase the viscosity of the suspension include, for example, sodium carboxymethyl cellulose, soribitol, and/or dextran. Optionally, the suspension may also contain stabilizers.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. For example, the present invention contemplates certain pro-drugs and derivatives of the above disclosed compounds, wherein

These compounds may be made by methods known in the art, i.e. the acetylation of the 1-hydroxy or 1-amino or 1-amido derivatives, etc., disclosed above, with the appropriate acid chloride or acid anhydride. $R^4$ may be

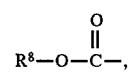

as well, when said 1-hydroxy, or 1-amino or 1-amido derivatives are reacted with the appropriate ortho ester. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

I claim:

1. A method of treating cardiovascular, pulmonary-respiratory, gastrointestinal, reproductive, allergic disease, shock and ocular hypertension which comprises administering an effective amount of a cyclopentane(ene) heptanoic or cyclopentane(ene) heptenoic acid, 2-hydrocarbylphosphinyloxymethyl or phosphonamidomethyl compound or derivative thereof represented by the formula I

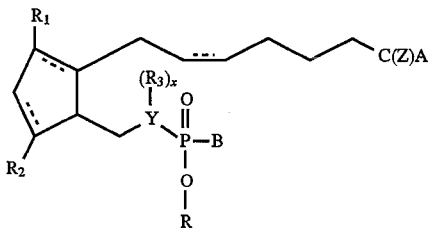

wherein the dashed bonds represent a single bond or a double bond which can be in the cis or trans configuration; A is a radical selected from the group consisting of

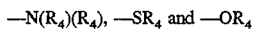

—N(R₄)(R₄), —SR₄ and —OR₄ wherein $R_4$ is hydrogen or $C_1$ to $C_3$ alkyl, Z is oxo or represents two hydrogen radicals, Y is O or N; x is 0 or 1, provided that x is 0 when Y is O and x is 1 when Y is N; B is an alkyl or an alkylcycloalkyl radical having from one to ten carbon atoms, or an arylalkyl radical, selected from the group consisting of hydrocarbyl arylalkyl and heteroarylalkyl radicals wherein the heteroatom is selected from the group consisting of nitrogen, oxygen and sulfur atoms and said arylalkyl radical may comprise up to twelve carbon atoms; R is selected from the group consisting of hydrogen; lower alkyl and alkenyl radicals having from 1 to 10 carbon atoms, aromatic radicals and heteroaromatic radicals having from 1 to 10 carbon atoms, wherein said heteroatom is selected from the group consisting of oxygen, nitrogen, and sulfur; and substituted derivatives thereof wherein said substituent is selected from the group consisting of halo, nitro, amino, thiol, hydroxy, alkyl, alkyloxy, alkyl carboxy and halo substituted alkyl radicals wherein said alkyl comprises from 1 to 3 carbon atoms, $R_3$ is hydrogen or a lower alkyl radical having from 1 to 3 carbon atoms; and one of $R_1$ and $R_2$ is =O, —OH or a —O(CO)R₆ group, and the other one is —OH or —O(CO)R₆, or $R_1$ is =O and $R_2$ is H, wherein $R_6$ is a saturated or unsaturated acyclic hydrocarbon group having from 1 to about 20 carbon atoms, or —(CH₂)ₘR₇ wherein m is 0–10; and $R_7$ is an aliphatic ring from about 3 to about 7 carbon atoms, or an aryl or heteroaryl ring, and pharmaceutically-acceptable salts thereof.

2. The method of claim 1 comprising administering a cyclopentane(ene) heptanoic or cyclopentane(ene) heptenoic acid, 2-(phenyl alkylphosphinyloxymethyl or phosphonamidomethyl) compound represented by the formula II

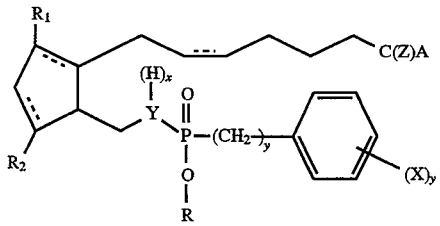

wherein y is 0, or an integer of from 1 to 4, X is a rascal selected from the group consisting of halo, nitro, amino, thiol, hydroxy, alkyl, alkyloxy and alkylcarboxy radicals wherein said alkyl comprises from 1 to 3 carbon atoms.

3. The method of treatment of claim 2 wherein said compound is a compound of formula (III).

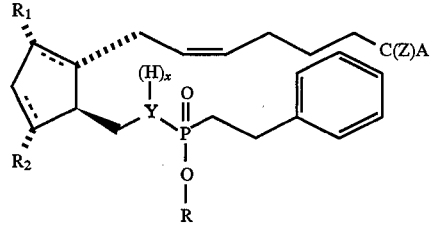

wherein hatched lines indicate α configuration, and a solid triangle indicates β configuration.

4. The method of claim 3 which comprises administering to a subject a pharmaceutical composition comprising a therapeutically effective amount of a cyclopentane heptenoic acid or derivative thereof of formula (IV)

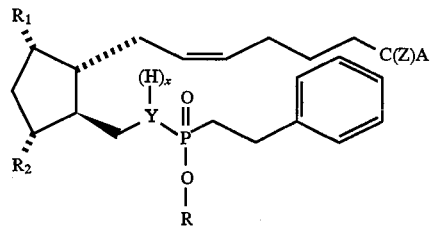

in combination with a pharmaceutical carrier.

5. The method of claim 4 wherein said compound is selected from compounds of the formula (V)

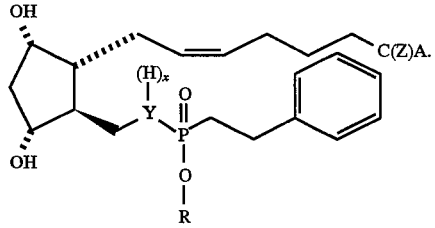

6. The method of claim 1 wherein B is selected from the group consisting of methyl, ethyl, propyl, butyl, pentyl, cyclopentylethyl, cyclohexylethyl, phenylethyl, thienylethyl, furanylethyl and pyridylethyl.

7. The method of claim 1 wherein Z is oxo.

8. The method of claim 7 wherein A is hydroxy or methoxy.

9. The method of claim 1 wherein said compound is selected from the group consisting of:

7-[3α,5α-Dihydroxy-2β-[[methoxy(2-phenylethyl)phosphinyl]oxymethyl]cyclopentyl]-5Z-heptenoic acid;

Methyl-7-[3α,5α-dihydroxy-2β-[[methoxy(2-phenylethyl)-phosphinyl]oxymethyl]cyclopentyl]-5Z-heptenoate;

7-[3α,5α-Dihydroxy-2β-[[methoxy(2-phenylethyl)phosphinyl]oxymethyl]cyclopentyl]-5Z-heptenol;

7-[3α,5α-Dihydroxy-2β-[[methoxy(2-phenylethyl)phosphinyl]oxymethyl]cyclopentyl]-5Z -heptenamide;

7-[3α,5α-Dihydroxy-2β-[[methoxy(2-phenylethyl)phosphinyl]oxymethyl]cyclopentyl]-5Z-N,N dimethyl heptenamide;

7-[3α,5α-Dihydroxy-2β-[[hydroxy(2-phenylethyl)phosphinyl]oxymethyl]cyclopentyl]-5Z-heptenoic acid;

7-[3α,5α-Dihydroxy-2β-[[ethoxy(2-phenylethyl) phosphinyl]oxymethyl]cyclopentyl]-5Z-heptenoic acid;

7-[3α,5α-Dihydroxy-2β-[(methoxy(2-phenylethyl) phosphonamido]cyclopentyl)methyl]-5Z-heptenoic acid;

Methyl-7-[3α,5α-dihydroxy-2β-[(methoxy(2-phenylethyl) phosphonamido)methyl]cyclopentyl]-5Z-heptenoate;

7-[3α,5α-Dihydroxy-2β-[(methoxy(2-phenylethyl) phosphonamido)methyl]cyclopentyl]-5Z-heptenol;

7-[3α,5α-Dihydroxy-2β-[(methoxy(2-phenylethyl) phosphonamido)methyl]cyclopentyl]-5Z-heptenamide;

7-[3α,5α-Dihydroxy-2β-[(methoxy(2-phenylethyl) phosphonamido)methyl]cyclopentyl]-5Z-N,N dimethyl heptenamide;

7-[3α,5α-Dihydroxy-2β-[(methoxy(2-phenylethyl) phosphonamido)methyl]cyclopentyl]-5Z-heptenyl methoxide acid;

7-[3α,5α-Dihydroxy-2β-[(hydroxy(2-phenylethyl) phosphonamido)methyl]cyclopentyl]-5Z-heptenoic acid;

7-[3α,5α-Dihydroxy-2β-[(ethoxy(2-phenylethyl) phosphonamido)methyl]cyclopentyl]-5Z-heptenoic acid; and 7-[3α,5α-Dihydroxy-2β-[(ethoxypentyl phosphinyl) oxymethyl]cyclopentyl]-5Z-heptenoic acid.

10. The method of claim 9 wherein said compound is

7-[3α,5α-Dihydroxy-2β-[[methoxy(2-phenylethyl) phosphinyl]oxymethyl]cyclopentyl]-5Z-heptenoic acid;

7-[3α,5α-Dihydroxy-2β-[(methoxy(2-phenylethyl) phosphonamido)methyl]cyclopentyl]-5Z-heptenoic acid; or Methyl-7-[3α,5α-dihydroxy-2β-[(methoxy(2-phenylethyl) phosphonamido)methyl]cyclopentyl]-5Z-heptenoate.

11. A composition useful for treating cardiovascular, pulmonary-respiratory, gastrointestinal, reproductive, allergic disease, shock and ocular hypertension which comprises administering an effective amount of a cyclopentane(ene) heptanoic or cyclopentane(ene) heptenoic acid, 2-hydrocarbylphosphinyloxy methyl or phosphonamidomethyl compound or derivative thereof represented by the formula I

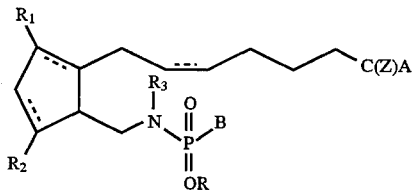

wherein the dashed bonds represent a single bond or a double bond which can be in the cis or trans configuration; A is a radical selected from the group consisting of —N(R₄)(R₄), —SR₄ and —OR₄ wherein R₄ is hydrogen or C₁ to C₃ alkyl. Z is oxo or represents two hydrogen radicals, Y is O or N; x is 0 or 1, provided that x is 0 when Y is O and x is 1 when Y is N; B is an alkyl or an alkylcycloalkyl radical having from one to ten carbon atoms, or an arylalkyl radical, selected from the group consisting of hydrocarbyl arylalkyl and heteroarylalkyl radicals wherein the heteroatom is selected from the group consisting of nitrogen, oxygen and sulfur atoms and said arylalkyl radical may comprise up to twelve carbon atoms; R is selected from the group consisting of hydrogen; lower alkyl and alkenyl radicals having from, 1 to 10 carbon atoms, aromatic radicals and heteroaromatic radicals having from 1 to 10 carbon atoms, wherein said heteroatom is selected from the group consisting of oxygen, nitrogen, and sulfur; and substituted derivatives thereof wherein said substituent is selected from the group consisting of oxygen, nitrogen, and sulfur; and substituted derivatives thereof wherein said substituent is selected from the group consisting of halo, nitro, amino, thiol, hydroxy, alkyl, alkyloxy, alkyl carboxy and halo substituted alkyl radicals wherein said alkyl comprises from 1 to 3 carbon atoms; R₃ is hydrogen or a lower alkyl radical having from 1 to 3 carbon atoms; and one of R₁ and R₂ is =O, —OH or a —O(CO)R₆ group, and the other one is —OH or —O(CO)R₆, or R₁ is =O and R₂ is H, wherein R₆ is a saturated or unsaturated acyclic hydrocarbon group having from 1 to about 20 carbon atoms, or —(CH₂)ₘR₇ wherein m is 0–10, and R₇ is an aliphatic ring from about 3 to about 7 carbon atoms, or an aryl or heteroaryl ring, and pharmaceutically-acceptable salts thereof.

12. A compound useful for treating cardiovascular, pulmonary-respiratory, gastrointestinal, reproductive, allergic disease, shock and ocular hypertension which comprises administering an effective amount of a cyclopentane(ene) heptanoic or cyclopentane(ene) heptenoic acid, 2-hydrocarbylphosphinyloxymethyl or phosphonamidomethyl compound or derivative thereof represented by the formula I

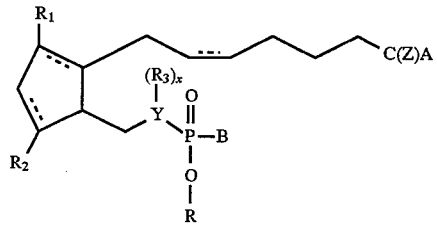

wherein the dashed bonds represent a single bond or a double bond which can be in the cis or trans configuration; A is a radical selected from the group consisting of —N(R₄)(R₄), —SR₄ and —OR₄ wherein R₄ is hydrogen or C₁ to C₃ alkyl. Z is oxo or represents two hydrogen radicals, Y is O or N; x is 0 or 1, provided that x is 0 when Y is O and x is 1 when Y is N; B is an alkyl or an alkylcycloalkyl radical having from one to ten carbon atoms, or an arylalkyl radical, selected from the group consisting of hydrocarbyl arylalkyl and heteroarylalkyl radicals wherein the heteroatom is selected from the group consisting of nitrogen, oxygen and sulfur atoms and said arylalkyl radical may comprise up to twelve carbon atoms; R is selected from the group consisting of hydrogen; lower alkyl and alkenyl radicals having from, 1 to 10 carbon atoms, aromatic radicals and heteroaromatic radicals having from 1 to 10 carbon atoms, wherein said heteroatom is selected from the group consisting of oxygen, nitrogen, and sulfur; and substituted derivatives thereof wherein said substituent is selected from the group consisting of oxygen, nitrogen, and sulfur; and substituted derivatives thereof wherein said substituent is selected from the group consisting of halo, nitro, amino, thiol, hydroxy, alkyl, alkyloxy, alkyl carboxy and halo substituted alkyl radicals wherein said alkyl comprises from 1 to 3 carbon atoms; $R_3$ is hydrogen or a lower alkyl radical having from 1 to 3 carbon atoms; and one of $R_1$ and $R_2$ is =O, —OH or a —O(CO)$R_6$ group, and the other one is —OH or —O(CO)$R_6$, or $R_1$ is =O and $R_2$ is H, wherein $R_6$ is a saturated or unsaturated acyclic hydrocarbon group having from 1 to about 20 carbon atoms, or —(CH$_2$)$_m$R$_7$ wherein m is 0–10, and $R_7$ is an aliphatic ring from about 3 to about 7 carbon atoms, or an aryl or heteroaryl ring, and pharmaceutically-acceptable salts thereof.

13. The compound of claim 12 wherein said compound is selected from compounds of the formula (V)

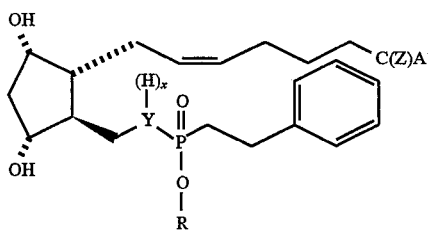

wherein hatched lines indicate α configuration and a solid triangle indicates a β configuration.

14. The compound of claim 12 wherein B is selected from the group consisting of methyl, ethyl, propyl, butyl, pentyl, cyclopentylethyl, cyclohexylethyl, phenylethyl, thienylethyl, furanylethyl and pyridylethyl.

15. The compound of claim 13 wherein Z is oxo.

16. The compound of claim 13 wherein said compound is selected from the group consisting of:

7-[3α,5α-Dihydroxy-2β-[[methoxy(2-phenylethyl)-phosphinyl]oxymethyl]cyclopentyl]-5Z-heptenoic acid;

Methyl-7-[3α,5α-dihydroxy-2β-[[methoxy(2-phenylethyl)-phosphinyl]oxymethyl]cyclopentyl]-5Z-heptenoate;

7-[3α,5α-Dihydroxy-2β-[[methoxy(2-phenylethyl) phosphinyl]oxymethyl]cyclopentyl]-5Z-heptenol;

7-[3α,5α-Dihydroxy-2β-[[methoxy(2-phenylethyl) phosphinyl]oxymethyl]cyclopentyl]-5Z-heptenamide;

7-[3α,5α-Dihydroxy-2β-[[methoxy(2-phenylethyl) phosphinyl]oxymethyl]cyclopentyl]-5Z-N,N dimethyl heptenamide;

7-[3α,5α-Dihydroxy-2β-[[hydroxy(2-phenylethyl) phosphinyl]oxymethyl]cyclopentyl]-5Z-heptenoic acid;

7-[3α,5α-Dihydroxy-2β-[[ethoxy(2-phenylethyl) phosphinyl]oxymethyl]cyclopentyl]-5Z-heptenoic acid;

7-[3α,5α-Dihydroxy-2β-[(methoxy(2-phenylethyl) phosphonamido]cyclopentyl)methyl]-5Z-heptenoic acid;

Methyl-7-[3α,5α-dihydroxy-2β-[(methoxy(2-phenylethyl) phosphonamido)methyl]cyclopentyl]-5Z-heptenoate;

7-[3α,5α-Dihydroxy-2β-[(methoxy(2-phenylethyl) phosphonamido)methyl]cyclopentyl]-5Z-heptenol;

7-[3α,5α-Dihydroxy-2β-[(methoxy(2-phenylethyl) phosphonamido)methyl]cyclopentyl]-5Z-heptenamide;

7-[3α,5α-Dihydroxy-2β-[(methoxy(2-phenylethyl) phosphonamido)methyl]cyclopentyl]-5Z-N,N dimethyl heptenamide;

7-[3α,5α-Dihydroxy-2β-[(methoxy(2-phenylethyl) phosphonamido)methyl]cyclopentyl]-5Z-heptenyl methoxide;

7-[3α,5α-Dihydroxy-2β-[(hydroxy(2-phenylethyl) phosphonamido)methyl]cyclopentyl]-5Z-heptenoic acid;

7-[3α,5α-Dihydroxy-2β-[(ethoxy(2-phenylethyl) phosphonamido)methyl]cyclopentyl]-5Z-heptenoic acid; and 7-[3α,5α-Dihydroxy-2β[(ethoxypentyl phosphinyl)oxymethyl]cyclopentyl]-5Z-heptenoic acid.

17. The compound of claim 16 wherein said compound selected from the group consisting of:

7-[3α,5β-Dihydroxy-2β-[[methoxy(2-phenylethyl) phosphinyl]oxymethyl]cyclopentyl]-5Z-heptenoic acid;

7-[3α,5α-Dihydroxy-2β-[(methoxy(2-phenylethyl) phosphonamido)methyl]cyclopentyl]-5Z-heptenoic acid; and Methyl-7-[3α,5α-dihydroxy-2β-[(methoxy(2-phenylethyl) phosphonamido)methyl]cyclopentyl]-5Z-heptenoate.

18. The compound of claim 17 wherein said compound is 7-[3α,5α-Dihydroxy-2β-[[methoxy(2-phenylethyl) phosphinyl]oxymethyl]cyclopentyl]-5Z-heptenoic acid.

19. The compound of claim 17 wherein said compound is Methyl-7-[3α,5α-dihydroxy-2β-[(methoxy(2-phenylethyl) phosphonamido)methyl]cyclopentyl]-5Z-heptenoate.

20. The method of claim 1 comprising administering the compound 7-[3α,5α-Dihydroxy-2β-[[methoxy(2-phenylethyl)-phosphinyl]oxymethyl]cyclopentyl]-5Z-heptenoic acid.

21. The method of claim 1 comprising administering the compound Methyl-7-[3α,5α-dihydroxy-2β-[(methoxy(2-phenylethyl)phosphonamido)methyl]cyclopentyl]-5Z-heptenoate.

* * * * *